(12) United States Patent
Guo et al.

(10) Patent No.: US 9,810,634 B2
(45) Date of Patent: Nov. 7, 2017

(54) METHOD FOR INHIBITING SELF-ABSORPTION EFFECT IN LASER-INDUCED BREAKDOWN SPECTROSCOPY

(71) Applicant: HUAZHONG UNIVERSITY OF SCIENCE AND TECHNOLOGY, Wuhan, Hubei (CN)

(72) Inventors: Lianbo Guo, Hubei (CN); Jiaming Li, Hubei (CN); Xiangyou Li, Hubei (CN); Xiaoyan Zeng, Hubei (CN); Yongfeng Lu, Hubei (CN); Rongxing Yi, Hubei (CN); Xinyan Yang, Hubei (CN); Zhongqi Hao, Hubei (CN)

(73) Assignee: Huazhong University of Science and Technology, Wuhan, Hubei (CN)

( * ) Notice: Subject to any disclaimer, the term of this patent is extended or adjusted under 35 U.S.C. 154(b) by 0 days.

(21) Appl. No.: 15/182,371

(22) Filed: Jun. 14, 2016

(65) Prior Publication Data

US 2017/0010215 A1    Jan. 12, 2017

(30) Foreign Application Priority Data

Jul. 7, 2015  (CN) .......................... 2015 1 0392450

(51) Int. Cl.
 G01J 3/30   (2006.01)
 G01N 21/71  (2006.01)

(52) U.S. Cl.
 CPC .......... *G01N 21/718* (2013.01); *G01N 21/71* (2013.01); *G01N 2201/06113* (2013.01)

(58) Field of Classification Search
 CPC ....... G01N 21/718; G01N 21/71; G01N 21/68
 See application file for complete search history.

(56) References Cited

U.S. PATENT DOCUMENTS 9,080,982 B1 *   7/2015   Asprey ................. G01N 21/68

* cited by examiner

*Primary Examiner* — Jamil Ahmed
(74) *Attorney, Agent, or Firm* — Hamre, Schumann, Mueller & Larson, P.C.

(57) ABSTRACT

Provided is a method for inhibiting self-absorption effect of a LIBS, comprising ablating a to-be-measured sample via a pulse laser thereby generating plasma, and selectively stimulating the plasma using a wavelength-tunable laser beam enabling transition of particles in a ground-state in the plasma to high energy state as stimulated absorption, thereby improving a stimulated absorption transition efficiency of the particles in a ground-state, and preventing plasma spectrum from being influenced by self-absorption effect. The invention is capable of eliminating the self-absorption effect without introducing external interference, obtaining original characteristics of emission spectrum from the center of the plasma, and essentially inhibiting and finally eliminating the self-absorption effect of laser plasma by making use of intrinsic physical property of plasma.

2 Claims, 4 Drawing Sheets

METHOD FOR INHIBITING SELF-ABSORPTION EFFECT IN LASER-INDUCED BREAKDOWN SPECTROSCOPY

TECHNICAL FIELD

The invention relates to the field of laser plasma emission spectrum, and more particularly, to a method for inhibiting self-absorption effect in laser-induced breakdown spectroscopy.

BACKGROUND OF THE INVENTION

Laser-induced breakdown spectroscopy (LIBS) is a kind of rapid component analysis technique. Basic principle of the LIBS technique is to focus a high-energy laser beam on surface of a to-be-measured sample so as to generating plasma by ablating, and then to obtain different types of elements of the sample and content thereof by analyzing plasma emission spectrum. Several unique advantages of the LIBS technique, such as simultaneous analysis of multiple elements, no sample preparation, in-situ detection, fast and remote detection and so on, make the technique continuously become a research hotspot, and be preliminarily applied in industries.

After fifty years' development, qualitative analysis of the LIBS technique has been widely recognized. However, analytical accuracy of the LIBS technique is lower than that of a conventional component analysis technique. At present, qualitative analysis has become an important and difficult research issue in the LIBS technique. As the LIBS technique employs laser as an excitation source, complexity of interaction between the laser and materials results in un-uniformity of temporal and spatial distribution of laser plasma, as well as light emission from particles in an excited state at the center of the laser plasma. As the light passes an outer layer, it is absorbed by particles in a ground-state of elements on the outer layer of the same type, and central intensity of a spectral line thereof is decreased and deformed, which is referred to as self-absorption effect. The self-absorption effect significantly affects emission light of the laser plasma, which causes quantitative accuracy of the LIBS technique to be poor. Therefore, negative effect of the self-absorption effect has to be eliminated so as to ensure accurate quantitative analysis of the LIBS technique.

Conventionally, there are two methods for weakening self-absorption effect of the laser plasma, the first one is to establish self-absorption mathematical models for correcting spectrum affected by self-absorption by processing experimental data and analyzing self-absorption effect of spectral lines; however, due to complexity of laser-induced plasma, the model can only correct part of self-absorption in spectrum, and thus this kind of methods has great limitation; the second one is to use special experimental environment or devices, and comprises changing a type of ambient gas, air pressure, spatial constraint of reflective mirrors and so on; but this kind of method can only be applicable for element detection under special conditions, which sacrifices fast detection of the LIBS technique in atmospheric environment useless.

SUMMARY OF THE INVENTION

In view of the above-mentioned problems, it is an objective of the invention to provide a method for inhibiting self-absorption effect in LIBS. This method is capable of eliminating the self-absorption effect without introducing external interference, obtaining original characteristics of emission spectrum from the center of the plasma, and essentially inhibiting and finally eliminating the self-absorption effect of laser plasma by making use of intrinsic physical property of plasma.

In accordance with an aspect of the invention, provided is a method for inhibiting self-absorption effect of a LIBS, comprising ablating a to-be-measured sample via a pulse laser thereby generating plasma, and selectively stimulating the plasma using a laser beam enabling transition of particles in a ground-state in the plasma to high energy state by stimulated absorption process, thereby improving a stimulated absorption transition efficiency of the particles in a ground-state, and preventing plasma spectrum from being influenced by self-absorption effect.

In a class of this embodiment, the method comprises steps of:

(1) determining a spectral line with a lower level of 0, a upper level of $E_1$ and a wavelength of $\lambda$ as an observation line, as well as another spectral line with a lower level of 0, a upper level of $E_2$ and a wavelength of $\lambda_1$ as an excitation line by searching in an atomic spectra database of a to-be-measured element in the to-be-measured sample, $E_2 \neq E_1$;

(2) ablating the to-be-measured sample to generate the plasma using a pulse laser;

(3) stimulating the whole plasma via wavelength-tunable laser with a wavelength of $\lambda_1$, and thus particles in a ground-state of the to-be-measured element in the plasma transits to the upper level of $E_2$; and (4) observating plasma emission spectrum with a wavelength of $\lambda$ emitted from the particles in the state $E_1$, thereby inhibiting self-absorption effect of the plasma emission spectrum.

In a class of this embodiment, a transition probability from a ground state 0 to the excitation line $E_2$ is above $10^5$ $s^{-1}$.

The method for inhibiting self-absorption effect of a LIBS of the invention can significantly inhibit or even eliminate the self-absorption effect of the LIBS technique, and improve qualitative analysis accuracy thereof. In addition, the invention essentially eliminates conditions under which the self-absorption is generated, and breaks through a bottleneck of qualitative analysis of the LIBS technique. Specifically, the invention features the following advantages:

(1) The invention essentially suppresses and eliminates the self-absorption effect without introducing external interference by making use of intrinsic physical property of plasma;

(2) being similar to an excitation source of the LIBS technique, the invention makes use of laser to suppress the self-absorption effect of plasma, and is superior to conventional methods in terms of remote detection, on-line analysis, no difference in analysis of a solid state, a liquid state and a gas state; and (3) the invention can eliminate distortion caused by self-absorption effect of emission light of the laser plasma, and improve accuracy and precision of qualitative analysis of the LIBS technique.

BRIEF DESCRIPTION OF ACCOMPANYING DRAWINGS

SPECIFIC EMBODIMENTS OF THE INVENTION

For clear understanding of the objectives, features and advantages of the invention, detailed description of the invention will be given below in conjunction with accompanying drawings and specific embodiments. It should be noted that the embodiments are only meant to explain the invention, and not to limit the scope of the invention.

Operation principle of a method for inhibiting self-absorption effect of a LIBS of the invention is, as a to-be-measured sample is ablated via a pulse laser and then a plasma is generated. The plasma is selectively simulated via a wavelength tunable laser. Since a wavelength of the wavelength-tunable laser can be continuously adjusted, the wavelength thereof is tuned to $\lambda_1$ ($\lambda_1$ is not equal to a wavelength $\lambda$ of a characteristic spectrum of the plasma). At the time, output photon energy corresponding to the wavelength $\lambda_1$ enables particles in a ground-state in the plasma to transit to a high energy state under stimulated absorption, which can significantly improve a stimulated absorption transition efficiency of the particles in the ground-state. Therefore, the number of particles in the ground-state rapidly decreases, thereby preventing self-absorption of a plasma emission spectrum at the center of the plasma, making it possible for an emission spectrum having a wavelength of $\lambda$ at the center of the plasma to pass through an outer region thereof, and effectively preventing self-absorption of laser plasma on the sample.

Figure 1:
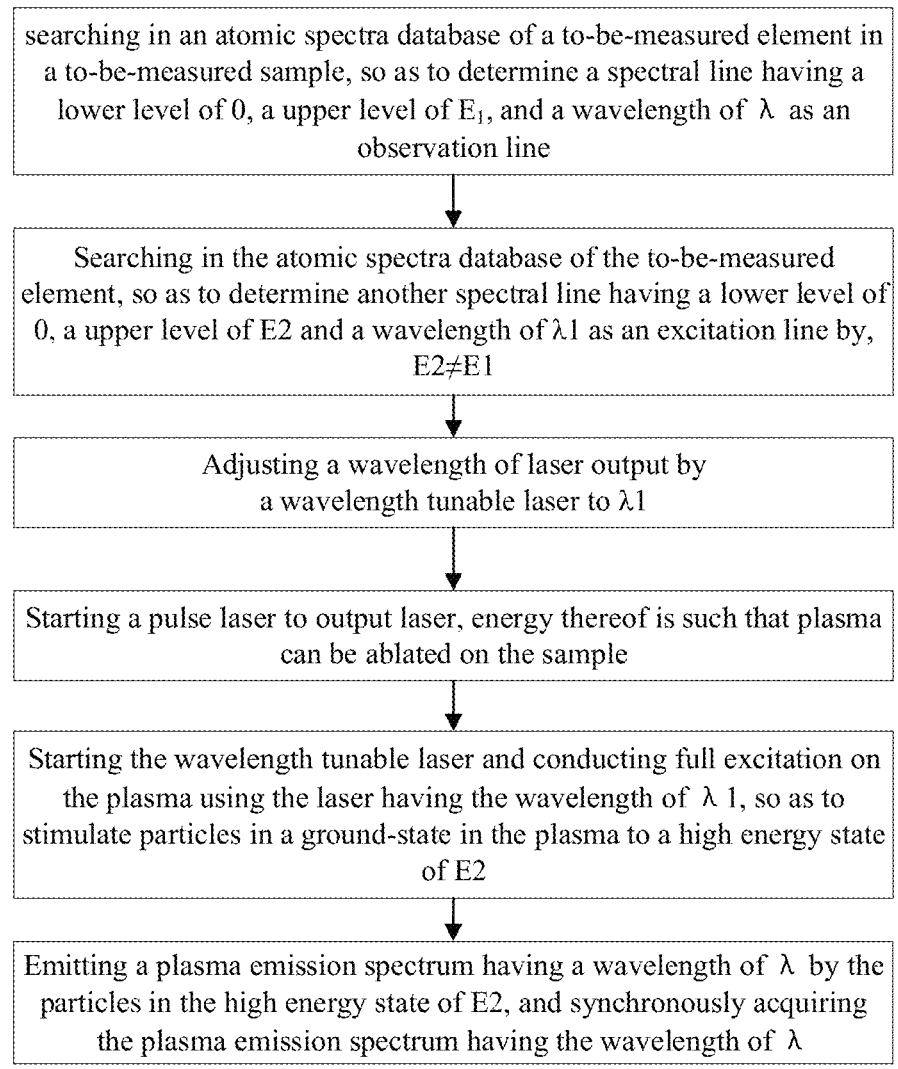
FIG. 1 is a flowchart of a method for inhibiting self-absorption effect of a LIBS of an exemplary embodiment of the invention.
Figure 2:
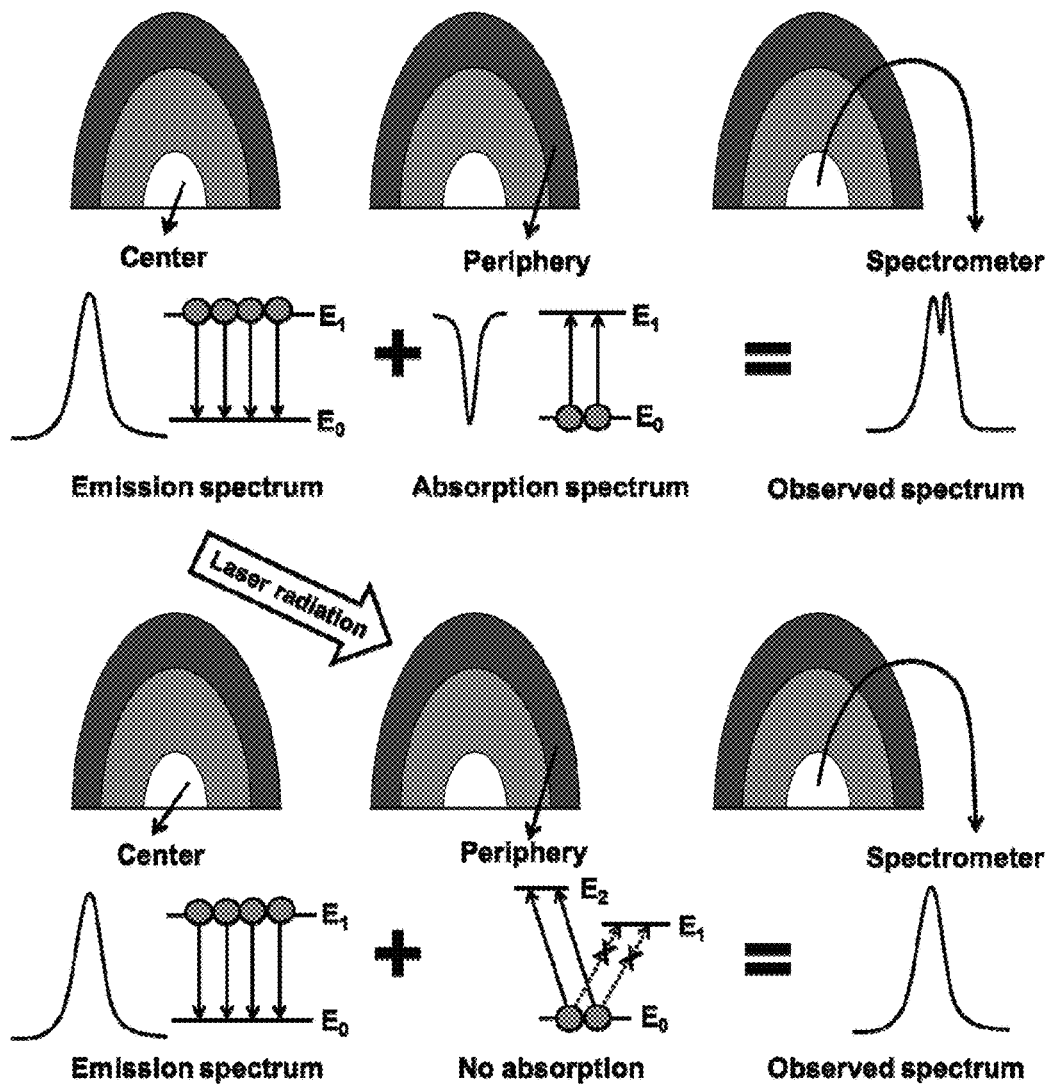
FIG. 2 illustrates selective stimulation of ground-state atoms under stimulated absorption transition in a plasma of the method of the invention.

As shown in FIG. 1, the method for inhibiting self-absorption effect of a LIBS of the invention comprises:

step 1: searching in an atomic spectra database of a to-be-measured element in a to-be-measured sample (the sample can be in any form such as solid, liquid or gas, and may contain any element) according to the to-be-measured element in the sample, so as to determine a spectral line having a lower level of 0 (a ground state), a upper level of $E_1$, and a wavelength of $\lambda$ as an observation line;

step 2: searching in the atomic spectra database of the to-be-measured element, so as to determine another spectral line having a lower level of 0, a upper level of $E_2$ and a wavelength of $\lambda_1$ as an excitation line by, $E_2 \neq E_1$, and a transition probability from a ground state 0 to the excitation line $E_2$ is above $10^5$ s$^{-1}$;

step 3: tuning the wavelength of laser output by a wavelength tunable laser to $\lambda_1$;

step 4: turning on a pulse laser to output laser, energy thereof is such that plasma can be ablated on the sample;

step 5: turning on the wavelength tunable laser and conducting full excitation on the plasma using the laser having the wavelength of $\lambda_1$, so as to stimulate particles in a ground-state in the plasma to a high energy state of $E_2$;

step 6: emitting a plasma emission spectrum having a wavelength of $\lambda$ by the particles in the high energy state of $E_1$, and synchronously acquiring the plasma emission spectrum having the wavelength of $\lambda$ via a spectrometer and a detector;

FIG. 2 illustrates principle of the method of the invention. In a conventional LIBS, light emitted from the center of a plasma is absorbed by particles in a ground-state of a similar element upon passing an outer region thereof, so center of a spectrum received by a detector is in the shape of a concave (as being affected by self-absorption). After using selective excitation of laser energy level of the invention, particles in a ground-state of same elements in the outer region of the plasma absorb laser photons, and are transitioned to the high energy state under stimulated absorption, and thus the number of particles in a ground-state generating self-absorption is significantly reduced. Therefore, spectrum emitted from the center of the plasma can directly pass through the outer region of the plasma, which prevents generation of the self-absorption effect, and facilitates effective inhibition thereof, and emitted spectrum acquired by the detector is in the shape of a peak.

Example 1

Next potassium in potassium bromide is used as an example to specifically explain the invention.

(1) two common-used analytical lines of potassium are K I 766.5 nm and K I 769.9 nm, which features strong self-absorption effect, resulting in self-reversal phenomenon. Severe spectral distortion may cause comparatively large errors of the two lines K I 766.5 nm and K I 769.9 nm during analysis. It can be known by searching in a NIST spectra database that a lower level of each of the two lines K I 766.5 nm and K I 769.9 nm is 0, upper levels thereof are respectively 1.62 eV 和 1.61 eV, and these two lines are used as observation lines;

(2) determining by searching the NIST spectra database that a transition energy level of the other spectral line K I 404.4 nm of potassium is 0~3.06 eV, selecting this spectral line as an excitation line;

(3) tuning a wavelength of laser output by the wavelength tunable laser to 404.4 nm;

(4) turning on the pulse laser and ablating plasma on surface of a potassium bromide sample;

(5) turning on the wavelength tunable laser and conducting full excitation on the plasma using the laser having the wavelength of 404.4 nm;

(6) respectively collecting the two lines K I 766.5 nm and K I 769.9 nm.

Figure 3:
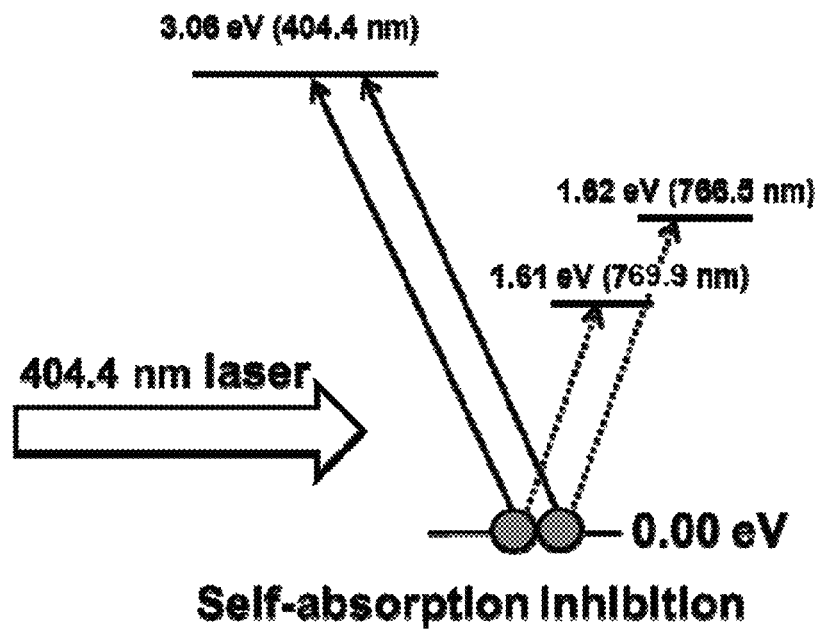
FIG. 3 illustrates inhabitation of self-absorption of two spectral lines of K I 766.5 nm and K I 769.9 nm.

As shown in FIG. 3, if the laser having the wavelength of 404.4 nm is not used, a large number of ground-state potassium atoms in the plasma may absorb light having wavelengths of 766.5 nm and 769.9 nm, and thus self-absorption effect may occur. If the laser having the wavelength of 404.4 nm is used, most ground-state potassium atoms in the plasma are stimulated and absorb the laser, and instantaneously transitioned to a high energy level of 3.06 eV, which makes it possible to significantly reduce the number of ground-state potassium atoms absorbing the analytical lines K I 766.5 nm and K I 769.9 nm, and thus inhibiting the plasma's capability of absorbing the analytical lines K I 766.5 nm and K I 769.9 nm, as well as the self-absorption effect.

Figure 4:
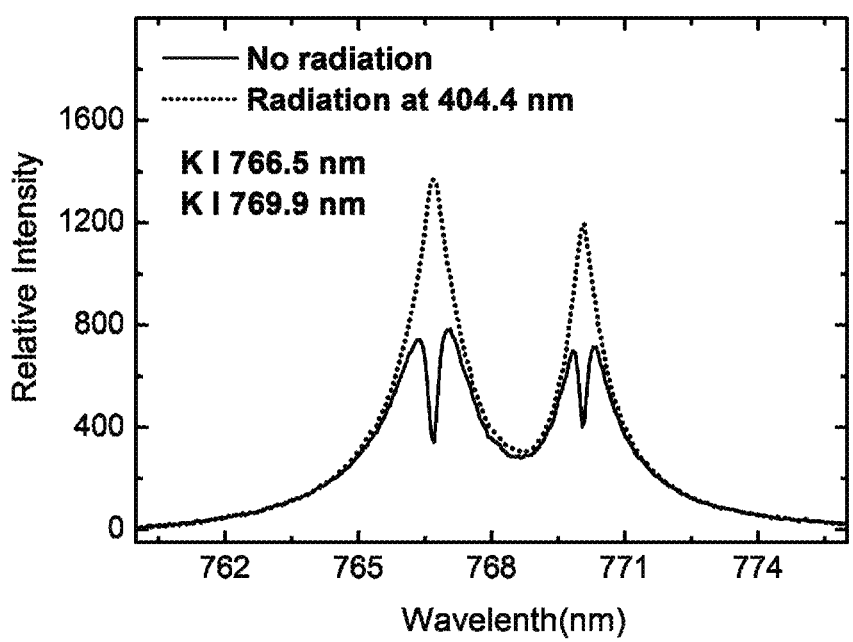
FIG. 4 illustrates results of inhibiting two spectral lines of K I 766 5 nm and K I 769.9 nm using the method of the invention.

FIG. 4 illustrates spectrum K I 766.5 nm and K I 769.9 nm of potassium atoms obtained by the method of the invention and a conventional method. It can be seen that the method of the invention can significantly inhibit the self-absorption of potassium atomic spectrum.

Example 2

Next aluminum in aluminum bronze is used as an example to specifically explain the invention.

(1) two common-used analytical line of aluminum are Al I 309.3 nm, which feature strong self-absorption effect, resulting in self-reversal phenomenon. Severe spectral distortion may cause comparatively large errors of the lines Al I 309.3 nm during analysis. It can be known by searching in a NIST spectra database that a lower level of the line Al I 309 3 nm is 0, a upper level thereof is 4.02 eV, and this line is used as observation lines;

(2) determining by searching the NIST spectra database that a transition energy level of the other spectral line Al I 394.4 nm of aluminum is 0~3.14 eV, selecting this spectral line as an excitation line;

(3) tuning a wavelength of laser output by the wavelength tunable laser to 394.4 nm;

(4) turning on the pulse laser and ablating plasma on surface of an aluminum bronze sample;

(5) turning on the wavelength tunable laser and conducting full excitation on the plasma using the laser having the wavelength of 394.4 nm;

(6) respectively collecting the two lines Al I 309.3 nm.

Figure 5:
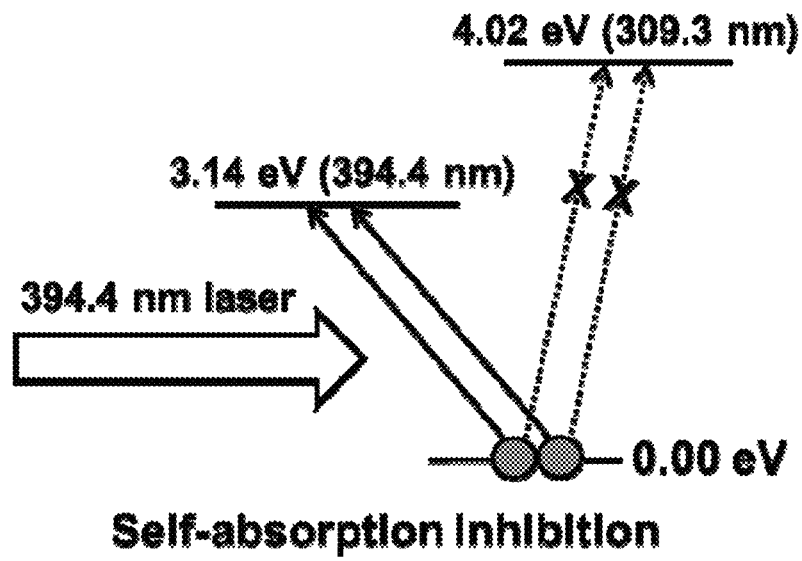
FIG. 5 illustrates inhabitation of self-absorption of a spectral line of Al I 309.3 nm.

As shown in FIG. 5, if the laser having the wavelength of 394.4 nm is not used, a large number of ground-state aluminum atoms in the plasma may absorb light having wavelengths of Al I 309.3 nm, and thus self-absorption effect may occur. If the laser having the wavelength of 394 4 nm is used, most ground-state aluminum atoms in the plasma are stimulated and absorb the laser, and instantaneously transitioned to a high energy level of 3.14 eV, which makes it possible to significantly reduce the number of ground-state potassium atoms absorbing the analytical line Al I 309.3 nm, and thus inhibiting the plasma's capability of absorbing the analytical line Al I 309.3 nm, as well as the self-absorption effect.

Figure 6:
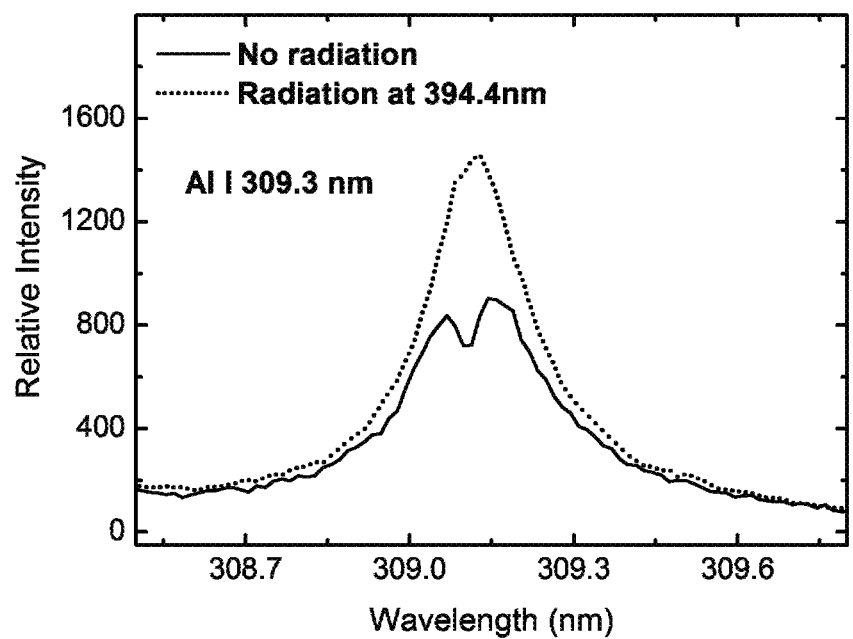
FIG. 6 illustrates results of inhibiting a spectral lines of Al I 309.3 nm using the method of the invention.

FIG. 6 illustrates spectrum Al I 309.3 nm of aluminum atoms obtained by the method of the invention and a conventional method. It can be seen that the method of the invention can significantly inhibit the self-absorption of potassium atomic spectrum.

While preferred embodiments of the invention have been described above, the invention is not limited to disclosure in these embodiments and the accompanying drawings. Any changes or modifications without departing from the spirit of the invention fall within the scope of the invention.

What is claimed is:

1. A method for inhibiting a self-absorption effect of laser-induced breakdown spectroscopy (LIBS), including ablating a to-be-measured sample via a pulse laser thereby generating plasma, and selectively stimulating the plasma using a wavelength-tunable laser beam enabling transition of particles in a ground-state in the plasma to a high energy state as stimulated absorption, thereby improving a stimulated absorption transition efficiency of the particles in the ground-state, and preventing the plasma spectrum from being influenced by the self-absorption effect, the method comprising:

determining a spectral line with a lower level of 0, an upper level of $E_1$, and a wavelength of $\lambda$ as an observation line, and determining another spectral line with a lower level of 0, an upper level of $E_2$, and a wavelength of $\lambda_1$ as an excitation line by searching in an atomic spectra database of a to-be-measured element in the to-be-measured sample, $E_2 \neq E_1$;

ablating the to-be-measured sample to generate the plasma using a pulse laser;

stimulating the plasma via a wavelength-tunable laser with a wavelength of $\lambda_1$, and thus particles in the ground-state of the to-be-measured element in the plasma transition to the upper level of $E_2$; and observing a plasma emission spectrum with a wavelength of $\lambda$ emitted from the particles in the ground-state in the upper level of $E_1$, thereby inhibiting the self-absorption effect of the plasma emission spectrum.

2. The method for inhibiting the self-absorption effect of a LIBS of claim 1, wherein a transition probability from a ground state 0 to the excitation line $E_2$ is above $10^5$ $s^{-1}$.

* * * * *

UNITED STATES PATENT AND TRADEMARK OFFICE
CERTIFICATE OF CORRECTION

| | | |
|---|---|---|
| PATENT NO. | : 9,810,634 B2 | Page 1 of 1 |
| APPLICATION NO. | : 15/182371 | |
| DATED | : November 7, 2017 | |
| INVENTOR(S) | : Guo et al. | |

It is certified that error appears in the above-identified patent and that said Letters Patent is hereby corrected as shown below:

On the Title Page

Item (72) The following inventor should be deleted:
"Yongfeng LU"

Signed and Sealed this
Second Day of June, 2020

Andrei Iancu
*Director of the United States Patent and Trademark Office*